(12) United States Patent
Gordon

(10) Patent No.: US 6,224,618 B1
(45) Date of Patent: May 1, 2001

(54) DEVICE FOR TREATMENT OF SPIDER VEINS

(76) Inventor: Dennis P. Gordon, 1244 Rancho Cir., Las Vegas, NV (US) 89107

( * ) Notice: Subject to any disclaimer, the term of this patent is extended or adjusted under 35 U.S.C. 154(b) by 0 days.

(21) Appl. No.: 09/421,611

(22) Filed: Oct. 20, 1999

(51) Int. Cl.[7] .................................................. A61B 17/34
(52) U.S. Cl. ............................................................ 606/185
(58) Field of Search ................................... 606/185, 159, 606/169, 170, 171, 180, 167

(56) References Cited

U.S. PATENT DOCUMENTS

| | | |
|---|---|---|
| 1,321,011 | 11/1919 | Cottes . |
| 3,581,688 | * 6/1971 | Ketterer ................. 122/224 |
| 4,185,634 | 1/1980 | Freedman . |
| 4,416,039 | 11/1983 | Miller . |
| 4,471,208 | * 9/1984 | Edmonds ............... 219/145.21 |
| 5,064,411 | 11/1991 | Gordon, III . |
| 5,522,844 | * 6/1996 | Johnson ................. 606/232 |
| 5,536,259 | 7/1996 | Utterberg . |
| 5,549,618 | 8/1996 | Fleenor et al. . |
| 5,769,866 | 6/1998 | Frantzen . |
| 5,792,168 | 8/1998 | Surval . |
| 5,893,858 | 4/1999 | Spitz . |
| 5,895,401 | 4/1999 | Daum et al. . |

FOREIGN PATENT DOCUMENTS

| | | |
|---|---|---|
| 3901 068 | 8/1989 | (DE) . |
| WO 94/21177 | 9/1994 | (WO) . |

* cited by examiner

*Primary Examiner*—Henry J. Recla
*Assistant Examiner*—Vy O. Bui
(74) *Attorney, Agent, or Firm*—Philip J. Anderson; Anderson & Morishita, LLC

(57) ABSTRACT

A device is set forth for treatment of spider veins. The device includes a needle having at its tip a slot defining tines. The needle is inserted through the skin to locate the spider vein in the slot. The needle is rotated to sever the vein from connecting veins.

9 Claims, 2 Drawing Sheets

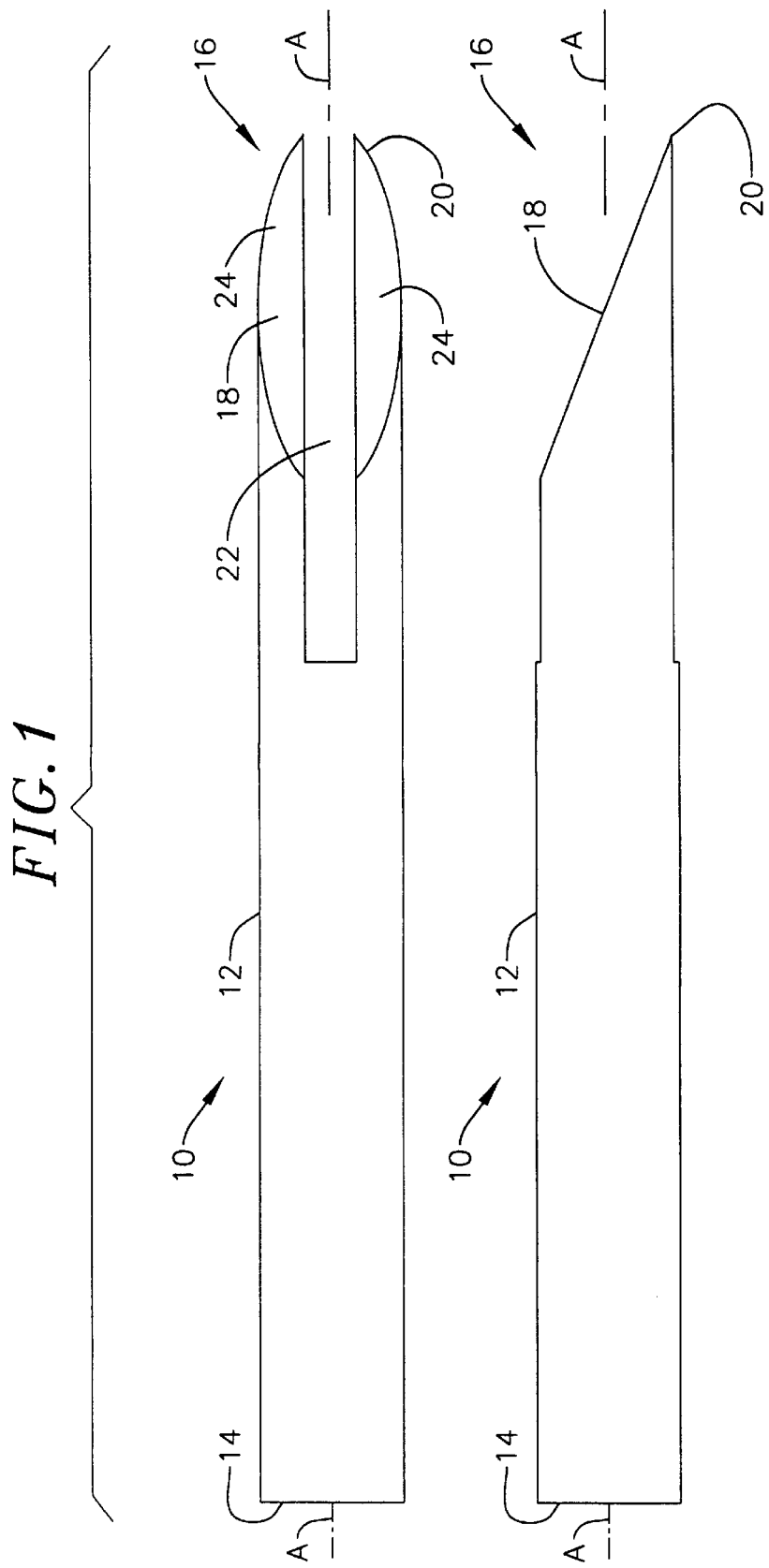

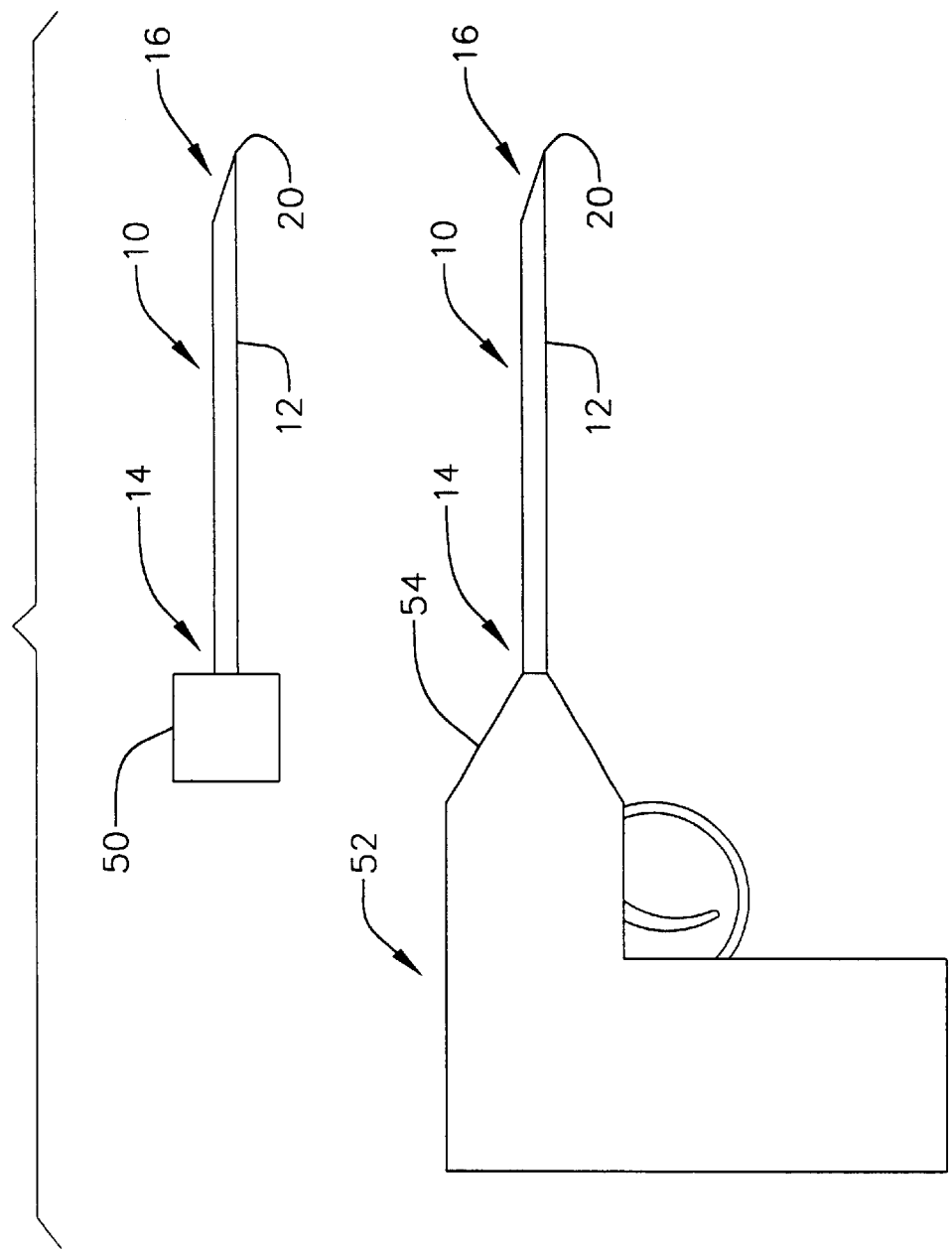

DEVICE FOR TREATMENT OF SPIDER VEINS

FIELD OF THE INVENTION

The present invention relates to medical devices and more particularly to devices for treatment of spider veins.

BACKGROUND

Spider veins, are a common cosmetic problem. They occur in approximately eighty million people, mostly Caucasian females. When severe they may be so unsightly as to deter the wearing of clothing such as shorts or skirts and may show through hosiery.

The cause is thought to be related to estrogen and/or venous insufficiency. Current treatment consists of sclerotherapy or laser treatment by cauterizing the veins. In Suval, U.S. Pat. No. 5,792,168 there is shown a device for treating varicose veins which includes a needle having a hook to capture the vein for removal from the incision. However, destroying the veins in situ does not work because veins will recannulize. Therefore, physically removing veins or interrupting their continuity appears to be the best hope for treatment.

SUMMARY OF THE INVENTION

There is provided according to the present invention a device and method for treatment of spider veins which includes providing a needle having a longitudinal axis and having at one end a tip shaped to puncture the skin. In this regard the tip may be beveled. The tip includes a slot to receive the spider vein to be treated. The needle is used to puncture the skin to locate the spider vein in the slot. Means are provided such as by providing a handle of a powered tool for axially rotating the needle to sever the spider vein. Once the vein is severed, the needle is withdrawn from the tissue. Because the spider vein is severed from connected veins, it no longer receives a blood supply and the severed vein dissolves or loses it red hue to no longer be visible. The puncture wound from the needle is small, is treated with sterile bandages and heals quickly without any significant scaring. Further because the puncture wound is small the risk if infection is minimized. By serially treating spider veins in a like manner, the discoloration of spider veins is eliminated or significantly reduced.

BRIEF DESCRIPTION OF THE DRAWINGS

These and other features and advantages will become appreciated as the same becomes better understood with reference to the description, claims and drawings where:

FIG. 1 shows the needle of the present invention in both a plan and elevation view, and FIG. 2 shows means for providing for the rotation of the needle

DESCRIPTION

Turning to FIG. 1 there is shown the device 10 according to one embodiment of the present invention. The device 10 preferably consists of a needle including a shank 12 having a first end 14 which may be adapted to be connected to a handle or a chuck of a powered instrument such a rotary powered device (not shown in FIG. 1) and a second end 16. The shank 12 is preferably cylindrical defining an axis A for the device 10 and may have a diameter of 0.030 inches, 0.040 inches or 0.050 inches. The shank 10 is preferably fashioned from surgical steel but it may also be fashioned from other rigid materials such as plastics. Where the device 10 is surgical steel it may be embodied as a surgical needle configured as hereinafter set forth below.

At the device 10 second end 16 there is provided means for puncturing the skin of the patient and for capturing a vein to be treated. These means are preferably embodied as including a bevel 18 which may be at 20 degrees with respect to the axis A and which defines a leading edge 20 for the device 10. These is also provided at the second end 16 from the leading edge 20 a slot 22 which extends diametrically through the shank 12 for, for example, about 0.150 inches. The width of the slot 22 may be approximately one-third the diameter of the shank 12 and defines thereby at the second end 16 tines 24 for the device 10.

To use the device 10, the patient is positioned to expose the area including the spider veins to be treated. The area of the spider veins may be anesthetized if desired. The device 10 is positioned to locate each spider vein to be treated to be received in the slot 22. The device 10 is then inserted through the skin with the leading edge 20 for each tine 24 penetrating the skin to straddle the vein to be treated and locate the vein in the slot 22. When so positioned, the shank 12 is rotated axially which pulls and breaks the vein trapped in the slot 22 from other, connected veins. The rotation of the shank 12 may be done manually by manipulation of the handle or by operation of a powered device attached to the shank 12. After the target vein has been severed, the shank 12 is withdrawn from the skin and moved to another target vein. This procedure is repeated until substantially all the desired spider veins have been targeted and severed. The area treated is then covered by bandage to prevent infection.

The severing of the spider veins decreases the chances of the spider vein veins recannulizing. Further the small holes formed by the shank 12 of the device 10 heal without any visible scar and without hospitalization or any significant outpatient care. The severed spider veins dissolve in the patients system or, because of the interruption of blood flow to the spider veins are no longer visible through the skin.

Turning to FIG. 2, the device 10 is shown with means for rotating the shank 12 which may be embodied as a simple handle 50 rotatable with the fingers or may be embodied as a powered tool 52 to which the shank first end 14 is removably coupled as by a chuck 54.

While I have shown and described certain embodiments of the present invention it is to be understood that it is subject to many variations without departing from the scope of the appended claims.

I claim:

1. A device for treatment of spider veins comprising:
   a solid needle having a substantially circular cross-section and a longitudinal axis and having at one end an ungular tip forming a substantially elliptical leading edge to puncture the skin, said tip including a slot extending to the leading edge to receive the spider vein to be treated;
   means for axially rotating the needle to sever the spider vein.

2. The device of claim 1 wherein the needle has a cylindrical shank and said slot has a span of approximately one-third the diameter of said shank.

3. The device of claim 2 wherein said slot is disposed axially.

4. The device of claim 1 wherein said rotating means includes a handle connected to the other end of said needle for manual rotation of said needle.

5. The device of claim 1 wherein said rotating means includes a powered device for selectively imparting rotation to the needle and means for removably coupling the needle other end to the powered device.

6. A method for treating spider veins comprising:

providing a solid needle having a circular cross section and a longitudinal axis and having at one end an ungular tip forming a substantially elliptical leading edge to puncture the skin, said tip including a slot extending axially to said leading edge to receive the spider vein to be treated;

inserting the tip to puncture the skin and locate the spider vein in the slot;

axially rotating the needle to sever the spider vein; and pulling the needle from the skin.

7. A device for treatment of spider veins comprising:

a needle having a longitudinal axis and having tip beveled at one side to define a bevel face having a, leading edge to puncture the skin, said tip including a slot defining tines to straddle the spider vein to be treated, said slot extending substantially the longitudinal length of the needle through the bevel face to the leading edge;

means for axially rotating the needle to sever the spider vein.

8. The device of claim 7 wherein said needle is cylindrical and said tip is ungular.

9. The device of claim 7 wherein the needle is solid.

* * * * *